(12) United States Patent
Leong

(10) Patent No.: US 8,173,008 B2
(45) Date of Patent: May 8, 2012

(54) METHOD FOR DETERMINING AN ANALYTE IN A BODILY FLUID SAMPLE USING AN ANALYTE TEST STRIP WITH COMBINATION ELECTRODE CONTACT AND METER IDENTIFICATION FEATURE

(75) Inventor: Koon-wah Leong, Sunnyvale, CA (US)

(73) Assignee: LifeScan, Inc., Milpitas, CA (US)

( * ) Notice: Subject to any disclaimer, the term of this patent is extended or adjusted under 35 U.S.C. 154(b) by 436 days.

(21) Appl. No.: 12/491,026

(22) Filed: Jun. 24, 2009

(65) Prior Publication Data

US 2010/0326846 A1 Dec. 30, 2010

(51) Int. Cl.
*G01N 27/26* (2006.01)
*G01N 33/50* (2006.01)

(52) U.S. Cl. .......... 205/792; 439/92; 439/211; 235/441; 235/446; 235/451; 235/482

(58) Field of Classification Search ..... 204/400–403.15; 205/792; 439/92, 211; 235/441, 446, 451, 235/482
See application file for complete search history.

(56) References Cited

U.S. PATENT DOCUMENTS

| | | | |
|---|---|---|---|
| 5,708,247 A | 1/1998 | McAleer et al. | |
| 5,951,836 A | 9/1999 | McAleer et al. | |
| 6,241,862 B1 | 6/2001 | McAleer et al. | |
| 6,270,637 B1 * | 8/2001 | Crismore et al. | 204/403.04 |
| 6,284,125 B1 | 9/2001 | Hodges et al. | |
| 6,716,577 B1 | 4/2004 | Yu et al. | |
| 6,814,844 B2 | 11/2004 | Bhullar et al. | |
| 6,827,829 B2 | 12/2004 | Kawanaka et al. | |
| 7,045,046 B2 | 5/2006 | Chambers et al. | |
| 2006/0189895 A1 * | 8/2006 | Neel et al. | 600/584 |
| 2007/0110615 A1 * | 5/2007 | Neel et al. | 422/57 |
| 2007/0227912 A1 * | 10/2007 | Chatelier et al. | 205/792 |
| 2009/0101523 A1 * | 4/2009 | Deng | 205/777.5 |

FOREIGN PATENT DOCUMENTS

WO  WO 2007/011569 A2  1/2007

\* cited by examiner

*Primary Examiner* — Jeffrey T Barton
*Assistant Examiner* — Jennifer Dieterle

(57) ABSTRACT

A method for determining an analyte in a bodily fluid sample includes inserting the analyte test strip into a test meter. The insertion is such that an electrical connector pin of the test meter travels along an electrical contact pad of the analyte test strip, and across a meter identification feature disposed on the electrical contact pad, during the insertion. Moreover, during the insertion, a signal processing module of the test meter measures an electrical characteristic via the electrical connector pin as the electrical connector pin travels along the electrical contact pad and across the meter identification feature. The method also includes identifying the analyte test strip, using the signal processing module, based on the electrical characteristic measured as the analyte test strip is inserted into the test meter and, thereafter, applying the bodily fluid sample to the analyte test strip upon notification by the test meter that the identification indicates that such applying is appropriate. The method then includes determining an analyte in the bodily fluid sample using the test meter only if the identification indicates that such determining is appropriate. The electrical contact pad of the analyte test strip employed in the method has a predetermined contact electrical characteristic value and the meter identification feature of the analyte test strip has a predetermined identification feature electrical characteristic value that is dissimilar from the predetermined contact electrical characteristic, thus providing for identification of the analyte test strip by the test meter.

12 Claims, 4 Drawing Sheets

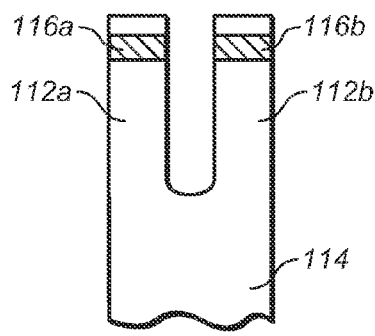
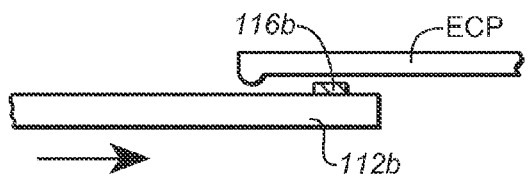
FIG. 3　　　FIG. 4
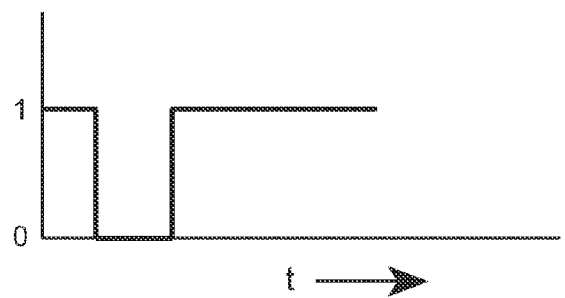
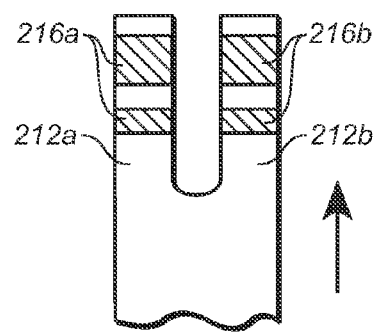
FIG. 5　　　FIG. 6
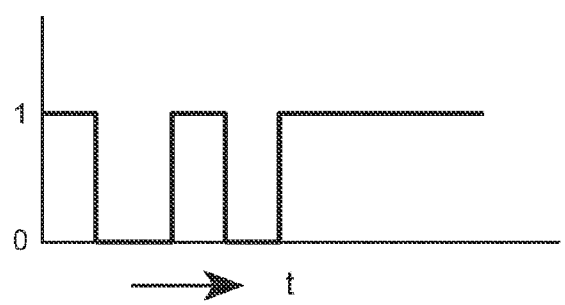
FIG. 7

METHOD FOR DETERMINING AN ANALYTE IN A BODILY FLUID SAMPLE USING AN ANALYTE TEST STRIP WITH COMBINATION ELECTRODE CONTACT AND METER IDENTIFICATION FEATURE

BACKGROUND OF THE INVENTION

1. Field of the Invention

The present invention relates, in general, to medical devices and, in particular, to analyte test strips, test meters and related methods.

2. Description of Related Art

The determination (e.g., detection and/or concentration measurement) of an analyte in a fluid sample is of particular interest in the medical field. For example, it can be desirable to determine glucose, cholesterol, acetaminophen and/or HbA1c concentrations in a sample of a bodily fluid such as urine, blood or interstitial fluid. Such determinations can be achieved using analyte test strips, based on, for example, photometric or electrochemical techniques, along with an associated test meter.

Typical electrochemical-based analyte test strips employ a plurality of electrodes (e.g., a working electrode and a reference electrode) and an enzymatic reagent to facilitate an electrochemical reaction with an analyte of interest and, thereby, determine the concentration of the analyte. For example, an electrochemical-based analyte test strip for the determination of glucose concentration in a blood sample can employ an enzymatic reagent that includes the enzyme glucose oxidase and the mediator ferricyanide. Such conventional analyte test strips are described in, for example, U.S. Pat. Nos. 5,708,247; 5,951,836; 6,241,862; and 6,284,125; each of which is hereby incorporated in full.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements, of which:

FIG. 3 is a simplified top view of combined electrical contact pads and meter identification features of the analyte test strip of FIGS. 1 and 2;

FIG. 4 is a simplified side view depiction of the combined electrical contact pads and meter identification features of FIG. 3 during insertion into a test meter, with an arrow indicating insertion direction, according to an embodiment of the present invention;

FIG. 5 is a simplified graph of an electrical characteristic (i.e., electrical continuity on the y-axis) versus time as detected by a test meter according to an embodiment the present invention during insertion of an analyte test strip that includes the combined electrical contact pads and meter identification features of FIG. 3;

FIG. 6 is a simplified top view of electrical contact pads and meter identification features of an analyte test strip according to another embodiment of the present invention with the arrow indicating direction of insertion into a test meter;

FIG. 7 is a simplified graph of an electrical characteristic (i.e., electrical continuity) versus time (also referred to as a graph of a time-dependent signal) as measured by a test meter according to an embodiment the present invention during insertion of an analyte test strip that includes the combined electrical contacts and meter identification features of FIG. 6;

DETAILED DESCRIPTION OF ILLUSTRATIVE EMBODIMENTS

Figure 1:
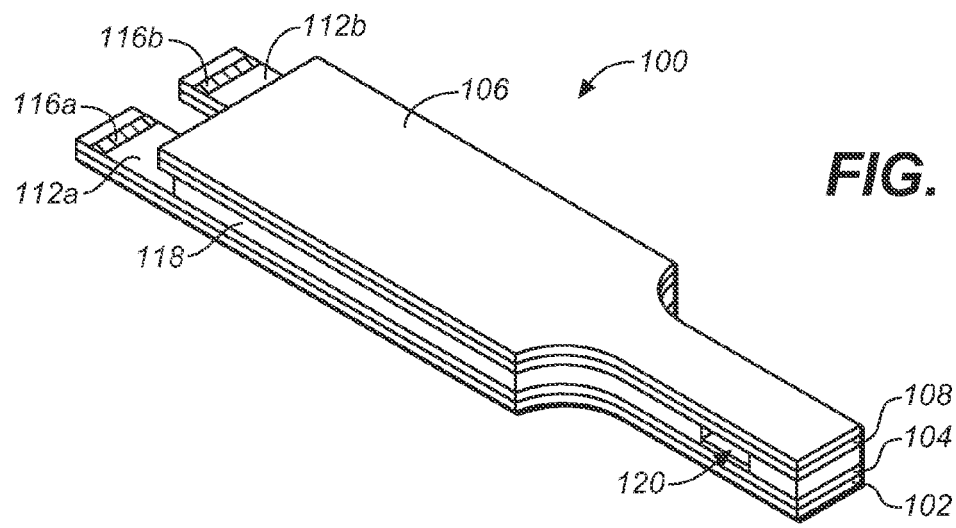
FIG. 1 is a simplified perspective depiction of an analyte test strip according to an embodiment of the present invention.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

In general, analyte test strips for use with a test meter (e.g., an electrochemical-based analyte test strip for determining glucose in a bodily fluid sample) according to embodiments of the present invention include a first insulating layer and an electrically conductive layer disposed on the first insulating layer. The electrically conductive layer includes at least one electrode portion and at least one electrical contact pad configured for an electrical connector pin of the test meter to travel therealong during insertion of the analyte test strip into the test meter. In addition, the electrical contact pad is in electrical communication with the electrode portion.

Analyte test strips according to embodiments of the present invention also include at least one meter identification feature disposed on the electrical contact pad such that the electrical connector pin of the test meter travels across the meter identification feature during insertion of the analyte test strip into the test meter. The analyte test strips further include a second insulating layer disposed above the first insulating layer and a patterned spacer layer positioned between the second insulating layer and the electrically conductive layer, the patterned spacer layer defining a sample-receiving chamber (for example, a bodily fluid sample receiving chamber) therein. The electrical contact pad of the analyte test strip has a predetermined contact electrical characteristic value and the meter identification feature has a predetermined identification feature electrical characteristic value that is dissimilar from the predetermined contact electrical characteristic.

Analyte test strips according to embodiments of the present invention can be readily identified by the test meter based on a measurement of the electrical characteristic, via the electrical connector pin, as the electrical connector pin travels along the electrical contact pad and across the meter identification pad. Such a measurement will generate a time-dependent signal of the electrical characteristic as the analyte test strip is inserted. The test meter employs the signal to identify the analyte test strip as either appropriate for use with the test meter or as inappropriate for use with the test meter. Such identification beneficially enables the test meter to proceed with analyte determination only when appropriate, thus avoiding potentially erroneous or inaccurate analyte determinations based on the use of unsuitable analyte test strips. The identification can occur by, for example, pattern matching the time-dependent signal to predetermined time-dependent signals of suitable analyte test strips or other suitable time-dependent signal analysis techniques. If desired, such pattern matching can accommodate variations in insertion speed by employing identification techniques that adjust for, or are independent of, insertion speed variation. These techniques can, for example, be based on the number of significant changes in the electrical characteristic (e.g., the number of interrupts in electrical continuity).

The meter identification feature of analyte test strips according to the present invention can, for example, be formed of a visually transparent material that renders them visually inconspicuous to a user and, therefore, beneficially non-distracting to the user. Such visually inconspicuous meter identification features enable a stealth identification of the analyte test strip by the test meter. In other words, the identification occurs without diverting the user's attention. Moreover, a variety of meter identification feature patterns can be employed from one analyte test strip batch to the next batch without bewildering or causing undue confusion to a user.

Figure 2:
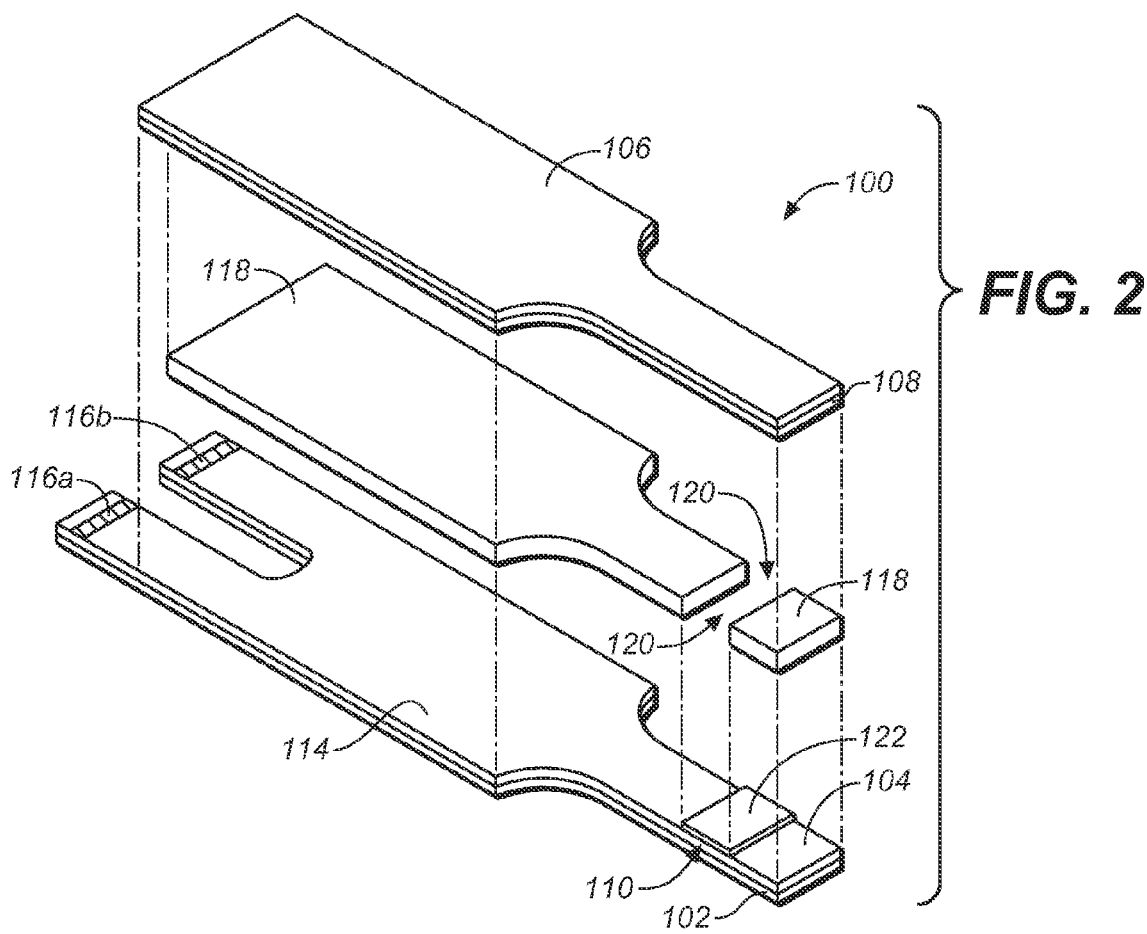
FIG. 2 is a simplified exploded perspective view of the analyte test strip of FIG. 1.

FIG. 1 is a simplified perspective depiction of an analyte test strip 100 for use with a test meter according to an embodiment of the present invention. FIG. 2 is a simplified exploded view of analyte test strip 100 and FIG. 3 is a simplified top view of combined electrical contact pads and meter identification features of analyte test strip 100. FIG. 4 is a simplified side view depiction of the combined electrical contact pads and meter identification features of analyte test strip 100 during insertion into a test meter, with an arrow indicating insertion direction. FIG. 5 is a simplified graph depicting a signal (namely, measured electrical characteristic [i.e., electrical continuity] versus time) as detected by a test meter according to an embodiment the present invention during insertion of analyte test strip 100 that includes the combined electrical contact pads and meter identification feature of FIG. 3.

Figure 8:
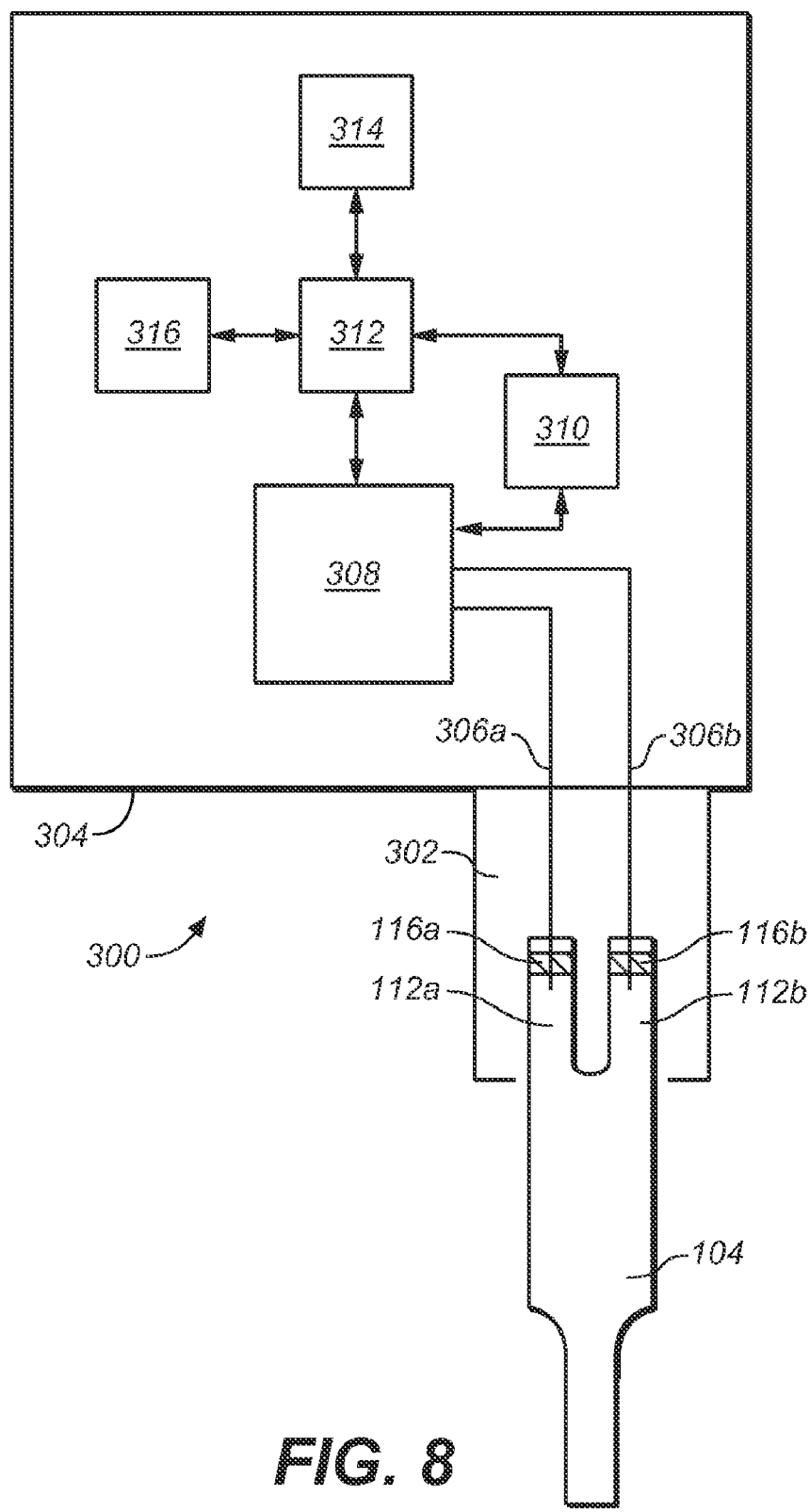
FIG. 8 is simplified depiction of the first conductive layer of an analyte test strip according to an embodiment of the present invention in use with a test meter also according to an embodiment of the present invention.

Referring to FIGS. 1-5, analyte test strip 100 for use with a test meter (described further herein, for example with respect to the embodiment of FIG. 8) according to an embodiment of the present invention includes a first insulating layer 102, with first electrically conductive layer 104 disposed thereon, and a second insulating layer 106, with second electrically conductive layer 108 disposed thereon. Second insulating layer 106 is disposed above first insulating layer 102.

First electrically conductive layer 104 includes first electrode portion 110 and electrical contact pads 112a and 112b. Electrical contact pads 112a and 112b are configured for an electrical connector pin (labeled ECP in FIG. 4) of the test meter to travel therealong during insertion of the analyte test strip into the test meter. Analyte test strip 100 also includes connection track 114 that provides electrical communication between electrical contact pads 112a and 112b and first electrode portion 110.

Analyte test strip 100 also includes meter identification features 116a and 116b disposed on electrical contact pads 112a and 112b such that the electrical connector pin (ECP in FIG. 4) of the test meter travels across meter identification features 116a and 116b during insertion of the analyte test strip into the test meter. In addition, electrical contact pads 112a and 112b are configured to operatively interface with an associated test meter.

In the embodiment of FIGS. 1-3, the electrical contact pads 112a and 112b have a predetermined contact electrical characteristic value and the meter identification features 116a and 116b have a predetermined identification feature electrical characteristic value that is dissimilar from the predetermined contact electrical characteristic.

Analyte test strip 100 also includes a patterned spacer layer 118 positioned between second insulating layer 106 and first electrically conductive layer 104. Patterned spacer layer defines a sample-receiving chamber therein 120. Analyte test strip 100 also includes a reagent layer 122, as depicted in FIGS. 1 and 2.

First insulating layer 102 and second insulating layer 106 can be formed, for example, of a plastic (e.g., PET, PETG, polyimide, polycarbonate, polystyrene), silicon, ceramic, or glass material. For example, the first and second insulating layers can be formed from a 7 mil polyester substrate.

In the embodiment of FIGS. 1-5, first electrode portion 110, along with a second electrode portion of second electrically conductive layer 108 (not shown in the FIGs for simplicity), are configured to electrochemically determine analyte concentration in a bodily fluid sample (such as glucose in a whole blood sample) using any suitable electrochemical-based technique known to one skilled in the art.

The first and second conductive layers, 104 and 108 respectively, can be formed of any suitable conductive material such as, for example, gold, palladium, carbon, silver, platinum, tin oxide, iridium, indium, or combinations thereof (e.g., indium doped tin oxide). Moreover, any suitable technique can be employed to form the first and second conductive layers including, for example, sputtering, evaporation, electro-less plating, screen-printing, contact printing, or gravure printing. For example, first conductive layer 104 can be a sputtered palladium layer and second conductive layer 108 can be a sputtered gold layer. A typical but non-limiting thickness for the first and second conductive layers is in the range of 5 nm to 100 nm.

Patterned spacer layer 118 serves to bind together first insulating layer 102 (with conductive layer 104 thereon) and second insulating layer 106 (with conductive layer 108 thereon), as illustrated in FIGS. 1 and 2. Patterned spacer layer 118 can be, for example, a double-sided pressure sensitive adhesive layer, a heat activated adhesive layer, or a thermo-setting adhesive plastic layer. Patterned spacer layer 118 can have, for example, a thickness in the range of from about 1 micron to about 500 microns, preferably between about 10 microns and about 400 microns, and more preferably between about 40 microns and about 200 microns.

Reagent layer 122 can be any suitable mixture of reagents that selectively react with an analyte such as, for example glucose, in a bodily fluid sample to form an electroactive species, which can then be quantitatively measured at an electrode of analyte test strips according to embodiments of the present invention. Therefore, reagent layer 122 can include at least a mediator and an enzyme. Examples of suitable mediators include ferricyanide, ferrocene, ferrocene derivatives, osmium bipyridyl complexes, and quinone derivatives. Examples of suitable enzymes include glucose oxidase, glucose dehydrogenase (GDH) using a pyrrolo-quinoline quinone (PQQ) co-factor, GDH using a nicotinamide adenine dinucleotide (NAD) co-factor, and GDH using a flavin adenine dinucleotide (FAD) co-factor. Reagent layer 122 can be using any suitable technique.

Meter identification features 116a and 116b are formed of a material with an electrical characteristic value (e.g., resistance, conductance, or capacitance) that is dissimilar from that electrical characteristic value of the electrical contact pads 112a and 112b. For example, the resistance of the meter identification features can be relatively high such that the meter identification features are essentially electrically non-conductive. In that circumstance, a time-dependent signal of electrical continuity measured via the electrical connector pins will have the form illustrated in FIG. 5 (where a y-axes value of "1" corresponds to electrical continuity between electrical connector pins traveling along electrical contact pads 112a and 112b and a y-axis value of "0" corresponds to electrical non-continuity as the electrical connector pins travel across the meter identification features). Although FIG. 5 employs a y-axis of electrical continuity, once apprised of the present disclosure, one skilled in the art will recognize that the time dependent signal could employ any suitable electrical characteristic or related electrical measurement (or combinations thereof) as the y-axes variable including electrical resistance, conductance, capacitance, measured voltage and measured current.

Suitable non-conductive materials that can be used for meter identification features in analyte test strips according to embodiments of the present invention include nonconductive UV, visible and IR cure adhesives materials, nonconductive solvent-based varnish materials, polyacrylate coating materials and polyurethane coating materials. Meter identification features can be formed using any suitable technique including, for example, inkjet printing, thermal transfer, syringe coating, slot coating, graviere coating, flexographic coating or screen printing techniques. A typical, but non-limiting, thickness for the meter identification feature(s) is in the range of 1 micron to 10 microns. The meter identification features can also include taggents, such as magnetic particles, which can be detected by a test meter as an additional means of identifying the analyte test strip.

Once apprised of the present disclosure, one skilled in the art will recognize that analyte test strips according to the present invention can have a variety of configurations. For example, U.S. patent application Ser. Nos. 12/464,935 and 12/145,314, which are hereby incorporated in full be reference, describe electrochemical-based analyte test strips that can be readily modified as embodiments of the present invention by the addition of at least one meter identification feature.

FIG. 6 is a simplified top view of electrical contact pads 212a, 212b and meter identification features 216a, and 216b of an analyte test strip according to another embodiment of the present invention with the arrow indicating direction of insertion into a test meter. The meter identification features of FIG. 6 are formed as a plurality of non-conductive stripes (in other words, high electrical resistance stripes) that extend across the highly conductive electrical contact pads (in other words low electrical resistance electrical contact pads). FIG. 7 is a simplified graph of an electrical characteristic (i.e., electrical continuity) versus time (also referred to as a time-dependent signal) as measured by a test meter according to an embodiment the present invention during insertion of an analyte test strip that includes the combined electrical contact pads and meter recognition features of FIG. 6.

In the embodiment of FIGS. 6 and 7, the non-conductive stripes (with a stripe width along the direction of electrical connector pin travel, for example, in the range of 100 microns to 4 millimeters) cause a break in electrical continuity that would otherwise exist between test meter electrical connector pins in contact with each of the two electrical contact pads 212a, and 212b. This lack of electrical continuity is measured (detected) by the test meter and represented by "0" level on the y-axis in FIG. 6, while electrical continuity is represented by a level of "1" in FIG. 6. The non-conductive stripes can have, for example, a relatively high electrical resistance in the range of 100 ohm/square to 10,000 ohms/square. The electrical contact pads can have, for example, an electrical resistance of approx. 10 ohm/square.

In general, test meters according to embodiments of the present invention are configured for use with an analyte test strip and include a test strip receiving module with at least one electrical connector pin and a signal processing module. The electrical connector pin is configured to (i) travel along an electrical contact pad of the analyte test strip during insertion of the analyte test strip into the test strip receiving module; and (ii) travel across a meter identification feature disposed on the electrical contact pad during insertion of the analyte test strip into the test meter. Moreover, the electrical contact pad has a predetermined contact electrical characteristic value and the meter identification feature has a predetermined identification feature electrical characteristic value that is dissimilar from the predetermined contact electrical characteristic. In addition, the signal processing module of the test meters is configured to measure an electrical characteristic (such as a time-dependent signal) via the electrical connector pin as the electrical connector pin travels along the electrical contact pad and across the meter identification pad.

FIG. 8 is simplified depiction of a test meter 300 according to embodiment of the present invention in use with a conductive layer of an analyte test strip according to an embodiment of the present invention (namely, analyte test strip 100 of FIGS. 1-5). Test meter 300 includes a test strip receiving module 302 and a signal processing module 304.

Test strip receiving module 302 includes two electrical connector pins 306a and 306b. Electrical connector pins 306a and 306b are configured to travel (ride) along the electrical contact pads 112a and 112b, respectively, during insertion of the analyte test strip into test strip receiving module 302. During such insertion, electrical connector pins 306a and 306b also travel across meter identification features 116a, and 116b disposed on electrical contact pads 112a and 112b, respectively.

Signal processing module 304 is configured to measure an electrical characteristic via electrical connector pins 306a and 306b as the electrical connector pins travel along electrical contact pads 112a and 112b and across the meter identification features 116a and 116b. Moreover, the electrical contact pad has a predetermined contact electrical characteristic value and the meter identification feature has a predetermined identification feature electrical characteristic value that is dissimilar from the predetermined contact electrical characteristic.

In the embodiment of FIG. 8, signal processing module 304 includes a test voltage unit 308, a current measurement unit 310, a processor unit 312, a memory unit 314, and a visual display 316 (see FIG. 8). The test meter 300 can measure, for example, electrical resistance, electrical continuity or other electrical characteristic between electrical connector pins 306a and 306b during use. One skilled in the art will appreciate that the test meter 300 can also employ a variety of sensors and circuits that are not depicted in simplified FIG. 8 during determination of an analyte. Moreover, test voltage unit 308, current measurement unit 310, processor unit 312, memory unit 314, and visual display 316 can also serve to perform additional test meter functions including, for example, the functions described in co-pending U.S. patent application Ser. No. 12/464,935, which is hereby incorporated in full by reference.

Figure 9:
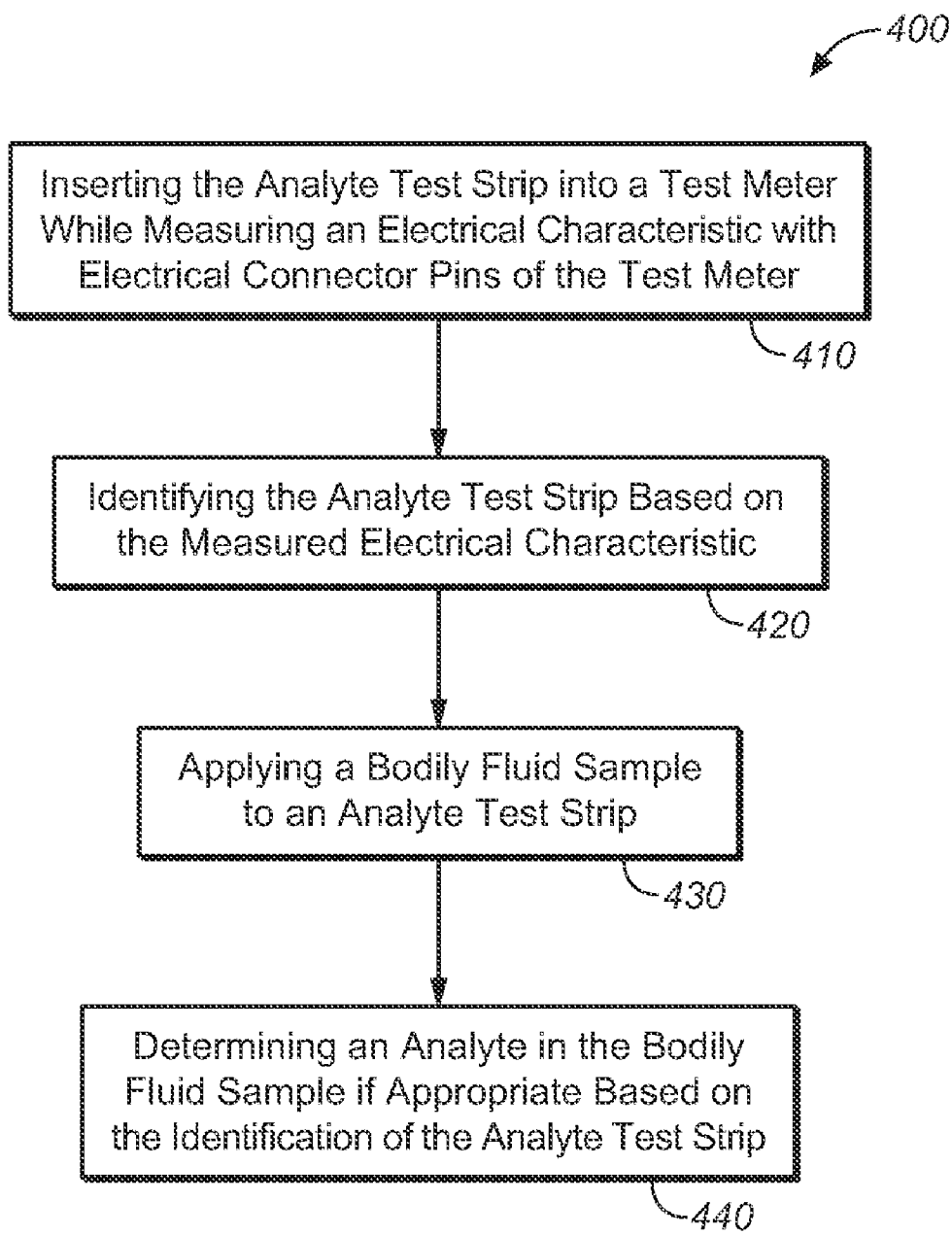
FIG. 9 is a flow diagram depicting stages in a process for determining an analyte in a bodily fluid sample according to an embodiment of the present invention.

FIG. 9 is a flow diagram depicting stages in a method 400 for determining an analyte in a bodily fluid sample according to an embodiment of the present invention. Method 400 includes, at step 410, inserting an analyte test strip into a test meter. Such insertion can occur at a rate, for example, in the range of 5 inches/second to 55 inches/second.

Insertion step 410 occurs such that at least one electrical connector pin of the test meter travels along at least one electrical contact pad of the analyte test strip, and also travels across a meter identification feature disposed on the electrical contact pad. In addition, during insertion step 410, a signal processing module of the test meter measures an electrical characteristic (e.g., one or more of electrical continuity between two electrical connector pins, resistance, conductance, and capacitance) via the electrical connector pin as the electrical connector pin travels along the electrical contact pad and across the meter identification feature. In method 400, the electrical contact pad has a predetermined contact electrical characteristic value and the meter identification feature has a predetermined identification feature electrical characteristic value that is dissimilar from the predetermined contact electrical characteristic. For example, the electrical contact pad can have a relatively low electrical resistance and the meter identification feature can have a relatively low resistance.

The signal processing module is then employed to identify the analyte test strip based on the electrical characteristic measured as the analyte test strip is inserted into the test meter, as set forth in step 420. For example, the electrical characteristic could have been measured as a time-dependent signal and the analyte test strip identified as either an appropriate strip for use with the test meter or an inappropriate strip for use with the test meter based on characteristics of that time dependent signal.

At step 430, a bodily fluid sample is applied to the analyte test strip if the test meter notifies a user that the identification indicates that such applying is appropriate. Such notification by the test meter can be, for example, an audible notification signal or a visual notification on a visual display of the test meter (for example, visual display 316 of the embodiment of FIG. 8). If the test meter indicates that applying a sample is not appropriate due to, for example, the analyte test strip being unsuitable for use with the test meter, the test meter will notify a user of such inappropriateness, thus discouraging a user from applying a bodily fluid sample to the test strip.

Subsequently, at step 440 and assuming that step 430 has resulted in a bodily fluid sample being applied to the test strip, an analyte (such as glucose) in the bodily fluid sample using is determined using the test meter only if the identification indicates that such determining is appropriate. Such a determination can be made, for example, using a suitable electrochemical technique wherein an electrochemical-based signal communicated from an electrode portion of the analyte test strip to the electrical connector pin of the test meter via the electrical contact pad with the meter identification feature thereon. In this manner, the same electrical contact pad is beneficially employed both during measurement of the electrical characteristic for identifying the analyte test strip and during analyte determination, thus minimizing the number of components needed in the analyte test strip and test meter and the number of potential failure points during use. Moreover, since a determination is only made when appropriate based on the identification, should a user erroneously apply a bodily fluid sample to a test strip after having been notified in step 430 that such application is inappropriate, a determination will not be made by the test meter. In addition, if application of the bodily fluid sample is done prior to insertion of the test strip into the test meter effectively eliminating step 430, a determination will not be made unless appropriate based on the identification.

Method 400 can be readily modified by one skilled in the art to incorporate any of the techniques, benefits and characteristics of analyte test strips according to embodiments of the present invention and described herein, as well as those of test meters according to embodiments of the present invention described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A method for determining an analyte in a bodily fluid sample, the method comprising:
   inserting an analyte test strip into a test meter such that:
      at least one electrical connector pin of the test meter travels along at least one electrical contact pad of the analyte test strip, and across a meter identification feature disposed on the electrical contact pad, during the insertion; and
      while a signal processing module of the test meter measures an electrical characteristic via the electrical connector pin as the electrical connector pin continuously travels along the electrical contact pad and across the meter identification feature,
   identifying the analyte test strip, using the signal processing module, based on the electrical characteristic measured as the analyte test strip is inserted into the test meter;
   determining an analyte in a bodily fluid sample applied to the test strip using the test meter only if the identification indicates that such determining is appropriate,
   wherein the electrical contact pad has a predetermined contact electrical characteristic value and the meter identification feature has a predetermined identification feature electrical characteristic value that is dissimilar from the predetermined contact electrical characteristic.

2. The method of claim 1 wherein the determining step includes determining the analyte based on an electrochemical-based signal communicated from an electrode portion of the analyte test strip to the electrical connector pin of the test meter via the electrical contact pad with the meter identification feature thereon.

3. The method of claim 1 wherein the signal processing module of the test meter measures the electrical characteristic as a time-dependent signal during the inserting step.

4. The method of claim 1 wherein determining step determines a glucose concentration in a blood sample.

5. The method of claim 1 wherein the meter identification feature is formed of an electrically insulating material.

6. The method of claim 1 wherein the meter identification feature is formed of a visually transparent material.

7. The method of claim 1 wherein the meter identification feature is formed as at least one stripe across the contact pad.

8. The method of claim 1 wherein there are two electrical contact pads; and wherein the analyte test strip is configured to provide a continuous conductive electrical circuit between the two electrical contact pads; and wherein the meter identification feature is formed of an electrically insulating material; and wherein the inserting step measures the electrical characteristic as electrical continuity.

9. The method of claim 1 wherein the meter identification feature is formed as a plurality of stripes across the contact pad.

10. The method of claim 1 further including the step, subsequent to the identifying step and prior to the determining step, of applying the bodily fluid sample to the analyte test strip upon notification by the test meter that the identification step indicates that such applying is appropriate.

11. The method of claim 1 wherein the meter identification feature includes a taggent detectable by the test meter during the inserting step.

12. The method of claim 11 wherein the taggent is magnetic and the inserting step includes detecting the magnetic properties of the meter identification feature.

* * * * *